United States Patent
Cleuziat et al.

[11] Patent Number: 5,824,517
[45] Date of Patent: Oct. 20, 1998

[54] METHOD FOR AMPLIFYING NUCLEIC ACID SEQUENCES BY STRAND DISPLACEMENT USING DNA/RNA CHIMERIC PRIMERS

[75] Inventors: Philippe Cleuziat, Lyons; Bernard Mandrand, Villeurbanne, both of France

[73] Assignee: Bio Merieux, Marcy-L'Etoile, France

[21] Appl. No.: 817,035

[22] PCT Filed: Jul. 24, 1996

[86] PCT No.: PCT/FR96/01166

§ 371 Date: May 16, 1997

§ 102(e) Date: May 16, 1997

[87] PCT Pub. No.: WO97/04126

PCT Pub. Date: Feb. 6, 1997

[30] Foreign Application Priority Data

Jul. 24, 1995 [FR] France ................................. 95 08945

[51] Int. Cl.[6] .............................. C12Q 1/68; C12P 19/34; C07H 21/04

[52] U.S. Cl. ........................... 435/91.2; 435/6; 435/91.1; 536/24.33

[58] Field of Search ............................ 435/6, 91.1, 91.2, 435/810; 536/24.33

[56] References Cited

U.S. PATENT DOCUMENTS

| | | | |
|---|---|---|---|
| 4,876,187 | 10/1989 | Duck et al. | 435/6 |
| 5,011,769 | 4/1991 | Duck et al. | 435/6 |
| 5,270,184 | 12/1993 | Walker et al. | 435/91.2 |
| 5,744,308 | 4/1998 | Guillou-Bonnici et al. | 435/6 |

FOREIGN PATENT DOCUMENTS

| | | |
|---|---|---|
| A2-0 500 224 | 8/1992 | European Pat. Off. |
| A3-0 667 393 | 8/1995 | European Pat. Off. |
| WO 92/00384 | 1/1992 | WIPO |
| WO 93/09250 | 5/1993 | WIPO |
| WO 95/03426 | 2/1995 | WIPO |

OTHER PUBLICATIONS

Derwent Publications Ltd., Database WPI, Section Ch, Week 9507, Class B04, AN 95–047919 (JP–A–06 327 500).

Proceedings of the National Academy of Sciences of USA, vol. 89, No. 1, Jan. 1, 1992, pp. 392–396, Terance Walker, "Isothermal in vitro amplification of DNA by a restriction enzyme/DNA polyermase system".

Genome Research (1995), vol. 5, No. 4, Nov. 1995, Hiroki Shibata et al., "RNA–primed PCR".

Walker et al., Nucleic Acids Res. 20(7), 1691–1696 (1992).

*Primary Examiner*—Kenneth R. Horlick
*Attorney, Agent, or Firm*—Oliff & Berridge, PLC

[57] ABSTRACT

A target nucleic acid may be amplified in the presence of an enzymatic system including DNA polymerase, strand translocation and RNAse H activities by using a chimeric primer that includes, in the 5' to 3' direction, an RNA-type segment capable of hybridizing with a 3'-terminal segment of the target and a DNA-type segment capable of hybridizing with a segment adjacent to the 3'-terminal segment of the target and a DNA- or RNA-type primer capable of hybridizing with the 3'-terminal segment of the target. A cyclic amplification that may be implemented isothermally on the basis of either a DNA or an RNA target is achieved even when the terminals are not defined.

13 Claims, 6 Drawing Sheets

METHOD FOR AMPLIFYING NUCLEIC ACID SEQUENCES BY STRAND DISPLACEMENT USING DNA/RNA CHIMERIC PRIMERS

FIELD OF THE INVENTION

The present invention relates to the amplification of nucleic acid sequences. In particular, the present invention relates to a process of nucleic acid amplification as well as the reagents to be used in this process.

DESCRIPTION OF RELATED ARTS

In nucleic acid and genetic material technologies, it is often necessary to determine whether a gene, a part of a gene, or a nucleotide sequence is present in a living organism, a cellular extract of this organism, or a biological sample. Since any gene or part of a gene is characterized by a specific sequence of nucleotide bases, one need only search directly for the presence of all or part of said specific sequence in a sample containing a mixture of polynucleotides.

There is enormous interest in this search for specific polynucleotide sequences, particularly in detection of pathogenic organisms, determination of the presence of alleles, detection of the presence of lesions in a host genome, or detection of the presence of a particular RNA or modification of a cell host. Genetic diseases such as Huntington's disease, Duchenne's disease, phenylketonuria, and β thalassemia can thus be diagnosed by analyzing nucleic acids from the individual. Also it is possible to diagnose or identify viruses, viroids, bacteria, fungi, protozoans, or any other form of plant or animal life by tests employing nucleic probes.

In the few examples cited above, once a specific sequence of an organism or a disease has been identified, the nucleic acids should be extracted from a sample and a determination should be made as to whether this sequence is present.

Various methods of nucleic acid detection have been described in the literature. These methods are based on the properties of purine-pyrimidine pairing of complementary nucleic acid strands in DNA-DNA, DNA-RNA, and RNA-RNA duplexes. This pairing process is effected by establishing hydrogen bonds between the adenine-thymine (A-T) and guanine-cytosine (G-C) bases of double-stranded DNA; adenine-uracil (A-U) base pairs can also form by hydrogen bonding in DNA-RNA or RNA-RNA duplexes. The pairing of nucleic acid strands for determining the presence or absence of a given nucleic acid molecule is commonly called "nucleic acid hybridization" or simply "hybridization."

The most direct method for detecting the presence of a target sequence in a nucleic acid sample is to obtain a "probe" whose sequence is sufficiently complementary to part of the target nucleic acid to hybridize therewith. The probe thus synthesized can be applied in a sample containing nucleic acids. If the target sequence is present, the probe will form a hybridization product with the target. In the absence of a target sequence, no hybridization product will form. If the synthesized probe is coupled with a detectable marker, the hybridization product can be detected by measuring the quantity of marker present. A transfer of the Southern (Southern, E. M., *J. Mol. Biol.*, 98, 503 (1975)) or Northern type or the dot-blot or hybridization sandwich technique (Dunn, A. R. and Hassel J. A., *Cell*, 12, 23, (1977)) are examples in which these methods are used.

The main difficulty in this approach, however, is that it is not directly applicable to cases where the number of copies of the target sequence present in a sample is small, less than approximately $10^7$. Under these conditions it is difficult to distinguish a significant signal, exceeding the background noise of the reaction (namely to distinguish specific attachment of a probe to its target sequence from nonspecific attachment of the probe to a sequence different from the target sequence). One of the solutions to this problem consists of augmenting the detection signal by a preliminary technique designed to specifically and considerably increase the number of copies of a target nucleic acid fragment if it is present in the sample. A technique of this type is currently called an amplification technique.

The articles by Lewis (1992, *Genetic Engineering News* 12: 1–9) and Abramson and Myers (1993, *Curr. Opin. Biotechnol.* 4: 41–47) are good general surveys of amplification techniques. The techniques are based mainly: a) either on repetition of DNA synthesis cycles in vitro by extension of nucleotide primers hybridized on the target sequence to be amplified by a DNA polymerase as in the method known as PCR (polymerase chain reaction, U.S. Pat. Nos. 4,683,195, 4,683,202, and 4,800,159; European Patent No. 0 201 184; or the technique known as RCR (repair chain reaction), Patent Application No. WO 90/01069; the strand displacement amplification method known as SDA, European Patent No. 0 497 272; or the exonuclease-mediated strand displacement amplification method, European Patent No. 0 500 224; b) or on the repetition of RNA synthesis cycles in vitro by a transcription reaction, by a DNA- or RNA-dependent RNA polymerase whose activity is necessarily associated with a specific region, known as a promoter region, containing a sequence or a structure playing the role of promoter (technique known as TAS, Patent Application No. WO 88/10315; technique known as 3SR (self-sustained sequence replication) described in Patent Application Wo 90/06995, and European Patent No. 0 373 960; the technique known as NASBA (nucleic acid sequence-based amplification) described in Patent Application Wo 91/02818 and European Patent No. 0 329 822; the technique known as SPSR (single primer sequence replication) described in U.S. Pat. No. 5,194,370; the ligation activated transcription method known as LAT, U.S. Pat. No. 5,194,370, and European Patent No. 0 369 775.

Nonetheless, all the aforementioned amplification techniques have at least one substantial limitation. They allow, for example, an amplification product to be obtained only from a single type of target nucleic acid: RNA or DNA. Another drawback to certain amplification techniques is the limitation in the size of the amplification reaction product. Techniques such as RCR or LCR allow only the target sequence corresponding to the primers and to the nucleotide probes used in the amplification method to be amplified. The nonspecific background noise (i.e. in the absence of the target) is also a serious drawback to certain techniques; thus, in the case of LCR, ligation of the ends of excess free oligonucleotides is effected in the absence of the target.

However, the critical point of all these amplification techniques resides in the step of template strand/newly synthesized amplified strand dissociation. In the techniques referred to above, the first solution proposed consists, as in PCR or RCR, of running numerous temperature cycles to dissociate the reaction products from the target and allow these products to serve as targets in their turn. This technical imperative consequently limits the choice of enzymes usable in amplification processes to heat-stable enzymes such as Taq polymerase in PCR or a heat-stable DNA ligase in RCR.

Moreover, the fact that successive temperature cycles are run is a drawback to automating these techniques.

The second solution proposed (see the 3SR, TAS, LAT, and NASBA techniques or the technique described in Patent Application No. EP 369 775) benefits from transcription systems via a DNA- or RNA-dependent RNA polymerase whose activity is necessarily associated with a promoter region. These systems have the advantage of being conductable under isothermal conditions because the transcription step releases single-stranded RNAs which in their turn can serve as targets. However, these amplification techniques too have numerous limitations. Thus, installation of a functional promoter region at the ends of the target sequences to be amplified is required for the transcription stage, often requires several steps prior to the transcription reaction proper, and brings in a cascade of enzyme activities. Hence it is very difficult to render these techniques efficient due to the difficulty of arriving at reaction conditions that simultaneously accommodate these four or five enzyme activities. Moreover, the creation of an operational promoter may, at each cycle, require installation of two oligonucleotides by ligation to the target, which also increases the number of steps (see for example the moving promoter process described in Patent Application EP 0369 775).

Finally, the SDA method proposes using the strand displacement property possessed by certain polymerases as a means of separating template from newly synthesized nucleic acid strands. This well-known property has been the subject of numerous scientific articles (see for example Y. Masamute and C.C. Richardson, 1971, J. Biol. Chem. 246, 2692–2701; R. L. Lechner et al., 1983, J. Biol Chem. 258, 11174–11184; or R. C. Lundquist and B. M. Olivera, 1982, Cell 31, 53–60). This amplification technique allows isothermal (37° C.) multiplication of a target DNA sequence with the aid of an appropriate restriction enzyme and a DNA-dependent DNA polymerase exempt of exonuclease activity (Walker et al, 1992. Proc. Natl. Acad. Sci. USA 89: 392–396). It is based on hybridization of oligonucleotide primers that have a recognition sequence for a restriction enzyme at their 5' end. After hybridization with the target, these primers are elongated by the DNA polymerase in the presence of at least one modified nucleotide (5'[α-thio] dNTP). The double-stranded DNA generated is subjected to the action of the specific restriction endonuclease. The presence of modified nucleotides on the newly synthesized DNA strand containing the specific sequence of the restriction endonuclease prevents this strand from being cleaved by the enzyme. Thus, a specific single-chain cleavage can be obtained on the primer leaving the modified complementary strand intact. DNA polymerase can then use the released 3' end to effect an extension along the target that has remained intact and release a single strand of DNA in the reaction medium because of the strand displacement property of the polymerase. This released strand can in its turn attach a primer containing a restriction enzyme fixation sequence and a cyclic reaction is then obtained. Likewise, European Patent Application 543 612 describes a process of preparing nucleic acids having defined ends, that can later serve in an amplification process, particularly the aforementioned SDA process. A process similar to SDA using exonuclease activity instead of an endonuclease and called "exonuclease-mediated strand displacement amplification" is described in European Patent No. 0 500 224.

However, the techniques described above are also limited. Firstly, the target sequence to be amplified must not include a restriction site corresponding to the endonuclease used in the process. Hence, it is essential to know, if not the total nucleic sequence of the fragment to be amplified, at least the restriction map of said fragment. Secondly, the choice of restriction nucleases is restricted to those that have the capacity of cleaving a hemiphosphorothioate recognition site (namely a site including a duplex strand with at least one modified phosphorothioate-type nucleotide) and, more generally, sites including modified nucleotides. Finally, in addition to constraints linked to the choice of modified nucleotide and chemical synthesis requirements, these amplification processes are also limited in yield since it is known that the Km of polymlerases for modified nucleotides is greater than that for natural nucleotides, so that the effectiveness of enzymatic incorporation of modified nucleotides into the target to be amplified is lower.

In view of these numerous drawbacks, it is hence desirable for novel amplification processes to become available.

Before describing the invention, certain terms used in the description will be defined below.

In the present application, the term "upstream" designates a region located at the 5' end of the nucleic acid or the polynucleotide sequence in question, and the term "downstream" designates a region located at the 3' end of said nucleic acid or said polynucleotide sequence.

A sequence "homologous" to another sequence designates a sequence identical to another or sufficiently identical to hybridize with a sequence strictly complementary to the sequence with which it is homologous.

The term "heteroduplex" designates an RNA/DNA hybrid. The term "homoduplex" designates a DNA/DNA or RNA/RNA hybrid.

An oligonucleotide sequence is said to be "of the DNA type" if it is made of DNA or if it is a modified polynucleotide sequence that, in addition to the hybridization properties of nucleic acid strands, possesses at least one other property in common with DNA. This common property will of course depend on the functionality of the modified sequence: it is in exercising this functionality that the sequence in question has a property in common with DNA (i.e., behaves like a DNA).

An oligonucleotide sequence is said to be of the "RNA type" if is made of RNA or if it is a modified polynucleotide sequence that, in addition to the hybridization properties of nucleic acid strands, possesses at least one other property in common with RNA, namely being sensitive to breakdown by RNAase H under the same conditions as RNA. It is known that RNAase H selectively breaks down the RNA strand of an RNA-DNA hybrid.

In the process according to the invention, the starting product includes a first segment "corresponding" to the sequence to be amplified, meaning that it is either said sequence to be amplified or a complementary strand to said sequence to be amplified, it being understood that in any event the process provides amplification of two complementary strands even when the starting product is single-stranded. It allows a useful nucleic acid to be obtained in the single-stranded form, facilitating its later application.

The displacement capacity of the strand, which is well known for certain polymerases, concerns, inter alia, synthesis of DNA by a DNA-dependent or RNA-dependent DNA polymerase. Of course, this strand displacement capacity is more effective when the polymerases concerned have no exonuclease 5'-3' activity. This strand displacement capacity can be provided independently of the polymerases, as described below. "Strand displacement activity" designates the phenomenon whereby a biological, chemical, or physical agent, for example a DNA polymerase, triggers dissociation of the complex formed by a nucleic acid template paired with its complementary strand, said dissociation progressing in a 5' to 3' direction in conjunction with progression of the synthesis of a new nucleic acid strand that complements the template. Strand displacement begins at the 5' end of a paired nucleic acid sequence and propagates downstream as nucleic acid synthesis progresses immediately upstream of the displacement site. The newly synthesized nucleic acid and the displaced nucleic acid generally have the same nucleotide sequence which is complementary to the template nucleic acid strand. The strand displacement activity can be supplied by the same enzyme as the enzyme conferring the nucleic acid synthesis activity, particularly DNA synthesis, or it can be a separate, independent activity. DNA polymerases such as $E.$ $coli$ DNA polymerase I, the Klenow fragment of DNA polymerase I, bacteriophage T7 or T5 DNA polymerase, HIV virus reverse transcriptase, or MMLV (Moloney murine leukemia virus) reverse transcriptase are enzymes that have both polymerase activity and strand displacement activity. Agents such as helicases can be used in conjunction with inducer agents that have no strand displacement activity to produce the strand displacement effect, namely displacement of a nucleic acid simultaneously with synthesis of a nucleic acid with the same sequence. Likewise, proteins such as Rec A or single-stranded binding proteins from $E.$ $coli$ or another organism can be used to produce or favor strand displacement in conjunction with other inducer agents. For further details and a discussion of strand displacement, reference may be made to Kornberg, A. and Baker, T. A., DNA Replication, $2^{nd}$ edition, pp. 113–225, Freeman, N.Y. (1992).

It should be noted that the polymerases used for effecting strand displacement can advantageously also be provided with ribonuclease H activity.

The terms "nucleic acid fragment," "nucleic acid segment," and "oligonucleotide" as used in the present application designate a natural DNA or RNA fragment, a natural or synthetic polynucleotide, an unmodified synthetic DNA or RNA fragment, or one that includes at least one modified base such as inosine, 5-methyldeoxycytidine, 5-dimethylaminodeoxyuridine, deoxyuridine, 2,6-diaminopurine, 5-bromodeoxyuridine, pseudouridine, pseudoisocytidine, or any other modified base allowing hybridization. This polynucleotide can also be modified at the internucleotide bond (such as phosphorothioate, H-phosphonate, or alkylphosphonate bonds) at the skeleton such as for example alpha-oligonucleotides (French Patent No. 2 607 507) or PNA (Egholm et al., 1992, $J.$ $Am.$ $Chem.$ $Soc.$ 114: 1895–1897). Each of these modifications can be taken in combination.

The term "solid substrate" as used here includes all materials on which a nucleic acid fragment can be immobilized for utilization in diagnostic tests, in affinity chromatography, and in separation processes. Natural materials, synthetic materials, whether or not they are porous or magnetic or chemically modified, can be used as the solid substrate, particularly polysaccharides such as cellulose materials, for example paper, cellulose derivatives such as cellulose acetate and nitrocellulose; polymers such as vinyl chloride, polyethylene, polystyrene, polyacrylate, or copolymers such as vinyl chloride and propylene polymer, vinyl chloride and vinyl acetate polymer; styrene-based copolymers; natural fibers such as cotton and synthetic fibers such as nylon; ceramics; silica. The substrates used in the present invention are a polystyrene polymer, a butadiene-styrene copolymer or a butadiene-styrene copolymer mixed with one or more polymers or copolymers chosen from polystyrene, styrene-acrylonitryl copolymers, or styrene-methylmethacrylate copolymers, polypropylenes, polycarbonates, or the like. Advantageously, the substrate of the present invention is a styrene-based polystyrene or copolymer including 10 to 90 wt. % styrene or silica groups. The solid substrates according to the invention can be, without limitation, in the form of a microtitration plate, a sheet, a cone, a tube, a well, beads, or the like.

The term "primer" designates a single-stranded oligonucleotide structure. These nucleotides can be deoxyribonucleotides and/or ribonucleotides. These nucleotides can be modified as described above in the paragraph in which the term "nucleic acid fragment" was defined. The oligonucleotide primers, once hybridized on a nucleic acid sequence (DNA, RNA or DNA-RNA chimeric molecule) that is substantially complementary are polymerase substrates. The 3'OH end of these substrates can be elongated, in the presence of adequate nucleotides and a polymerase, leading to synthesis of a strand complementary to the template sequence on which said primer is hybridized. A primer can also be constituted by hybridizing the end of a single-stranded nucleic acid sequence on itself, leading in particular to formation of hairpin or stem-loop structures. The oligonucleotide primers hybridized on a nucleic acid sequence have the property of attaching the polymerases to their 3'OH end.

SUMMARY OF THE INVENTION

The present invention provides a process for amplifying a sequence of target nucleic acid (RNA and/or DNA) (as well as its complementary sequence) that advantageously combines the use of chimeric primers and the property of certain displacing polymerases. The sequence to be amplified can be any sequence. This process has the advantages of being implementable isothermally, allowing the use of a single enzyme combining the three enzyme activities required (this is the case in particular of reverse transcriptase), and being accomplishable from either a DNA or an RNA target even when the ends are not defined. In addition, it does not involve incorporation of nucleotides modified in the amplification products by the polymerases used.

Hence the invention relates to a process of amplification of a target nucleic acid sequence, said sequence including, starting from its 5' end, an upstream region, and, starting from its 3' end, a downstream region, said process including the steps consisting of:
obtaining a DNA-type single-stranded polynucleotide including a first segment corresponding to the target sequence to be amplified and also including a second segment of arbitrary sequence located downstream of the 3' end of said first segment, and
placing said single-stranded polynucleotide in contact, in the presence of an enzyme system with DNA-dependent DNA polymerase activity, strand displacement activity, and RNAase H activity, and in the presence of excess deoxyribonucleotide triphosphates,
with a set of primers, present in excess, including:
a) a first chimeric primer including successively, in the 5'→3' direction:
an RNA-type segment with a sequence complementary to at least part of the sequence of the second segment of said single-stranded polynucleotide, said part including the 5' end of said second segment,
and a DNA-type segment capable of hybridizing with at least part of said downstream region, said part containing the 3' end of said downstream region, and/or b) a second chimeric primer including successively, in the 5'→3' direction
   an RNA-type segment of arbitrary sequence,
   and a DNA-type segment homologous with at least part of said upstream region, said part containing the 5' end of said upstream region,
it being understood that:
   either the first primer contains, upstream of the RNA-type segment, a second DNA-type segment of arbitrary sequence, but at least part of which containing its 3' end is capable of hybridizing with a part containing the 3' end of said polynucleotide when said RNA segment is shorter than said second segment of said single-stranded polynucleotide,
   or the first primer does not contain such a second DNA-type segment and, in this case, said set of primers then contains a third primer of which at least a part, containing the 3' end of said third primer, is capable of hybridizing with at least part of the second segment of said single-stranded polynucleotide,
it being understood that:
   either the second primer contains, upstream of the RNA-type segment, a second DNA-type segment of arbitrary sequence,
   or the second primer does not contain such a second DNA-type segment and in this case said set of primers includes a fourth primer of which at least one part, containing the 3' end of said fourth primer, is homologous with at least a part of the sequence of the RNA-type segment of the second primer.

As will be seen in the discussion hereinbelow of the attached drawings, the third and fourth primers can be of the DNA type or of the RNA type.

The starting products used in the process that has just been defined can be prepared either by synthesis or by hemisynthesis, or according to the different "pathways of entry" described below.

With reference to the attached drawings, flowcharts of the process according to the invention will be described hereinbelow with certain starting products and/or certain particular primers. It is easy to verify that all the starting products (targets) and/or primers as defined above can give rise to an amplification reaction according to the invention.

The various segments present in the primers, which may pair with the target or the products deriving therefrom and then prime the synthesis of a nucleotide strand in the process of the invention are long enough to permit extension by a polymerase. This sufficient length may be determined in each case by simple routine experiments. The length is at least two nucleotides and preferably at least five nucleotides. These conditions are valid particularly for the DNA-type segments of the first and second primers; for the third and fourth primers; and for the fifth and sixth primers that will be defined hereinbelow. The same minimum conditions also of course apply for the segments, regions, or zones of the target polynucleotide (and of the various polynucleotides formed during the process of the invention) that may hybridize with these primers or primer segments.

The RNA-type segment of the first and second primers contains at least one ribonucleotide, particularly at least two ribonucleotides and for example at least four ribonucleotides.

In one particular embodiment of the invention, in order to limit the number of nucleotide primers used in the present invention, the first and second chimeric primers may be chosen to be identical or partially identical. In particular, their respective RNA-type segments can be identical. Likewise, their second (optional) DNA-type segments may be identical if they are present. Moreover, the third and fourth primers may be identical and may in particular be homologs of the RNA-type segment of the first and/or second primers.

According to one particular embodiment, the original target nucleic acid can be a DNA or an RNA isolated from a biological sample. In this case, it is possible to have an amplification reaction as defined above, starting from the target nucleic acid, by adding all the necessary reagents (primers, polymerase, etc.) at the very start of the reaction, and possibly after denaturing the target. This particular embodiment is characterized in that, to obtain said DNA-type single-stranded polynucleotide used as the starting product in the process defined hereinabove, one begins with a target nucleic acid containing the sequence to be amplified, extended, beyond the 3' end of said sequence to be amplified, by a downstream polynucleotide segment containing a oligonucleotide zone known as "upstream," and possibly extended beyond the 5' end of said sequence to be amplified by an upstream polynucleotide segment, said target nucleic acid is placed in contact with an excess of deoxyribonucleotide triphosphates and in the presence:
   of said system with DNA polymerase, strand displacement, and RNAase H activities;
   and of a set of primers containing primers as defined above and additionally containing a fifth primer (C1) capable of hybridizing with said downstream zone of the target. It is also possible to add a sixth primer (C2) homologous with an oligonucleotide zone, called upstream zone, of said upstream polynucleotide segment, and hence capable of hybridizing with a sequence complementary to said upstream zone. Of course, all the reagents can be mixed at the outset and the cyclic amplification reaction occurs once the single-stranded polynucleotide is obtained, defined above as the starting product, with no particular operating step.

According to another embodiment, the starting product is an RNA containing the sequence to be amplified. In this case, to obtain said DNA-type single-stranded polynucleotide, it is sufficient to place said starting RNA in contact with said first and second primers and where applicable with said third and fourth primers.

Another subject of the invention is a kit for implementing the amplification process described above for detecting any target nucleic acid present in a sample.

The target nucleic acid may be isolated from a sample of any starting material suspected of containing it. For animals, particularly mammals, the origin of these materials may be blood, bone marrow, lymph, hard tissue (liver, spleen, kidney, lung, ovaries, etc.), sputum, smears, feces, urine, sperm, etc. Other origins of starting materials may be plants, soil samples, food, and any other source suspected of containing biological organisms.

The nucleic acids may be isolated from these starting materials by various known methods not described here.

As soon as the nucleic acids are isolated they may be subjected to summary fragmentation by means such as ultrasonic treatment to obtain fragments less than 10 kilobases in size. This facilitates initial denaturing, particularly in the case of a double-stranded nucleic acid.

The target nucleic acid fragments thus obtained are denatured, where applicable, to make them single-stranded and allow hybridization of primers A1 and C1 and, if the initial nucleic acid is double-stranded, A2 or C2 (or vice versa). Primers A1, A2, C1, and C2 are defined above in the description of the flowcharts in the attached drawings. It is preferable to raise the temperature to approximately 95° C. for denaturing, but the strands can also be separated by increasing the pH then neutralizing the medium to allow primers to hybridize on the target. Before or after the target nucleic acids are denatured, a reaction mixture containing excess deoxyribonucleotide triphosphates, appropriate primers, and a mixture of DNA polymerase, strand displacement, and RNAase H enzymatic activities is added. If a temperature rise is used to denature the target nucleic acids, unless thermostable enzymes are used, it is preferable to add the enzymes after denaturing. The reaction mixture needed for accomplishing the amplification reaction according to the invention can also contain for example polyols such as glycerol, sorbitol, and polyethylene glycol or denaturing agents and/or solvent such as dimethylformamide, dimethylsulfoxide (DMSO), stabilizing agents such as albumin, sugars such as trehalose or mannose, etc. These reagents reduce any nonspecific hybridization reactions that could generate background noise.

The polymerases used in the process of the invention are preferably those with strand displacement activity. This activity is a well-known property of certain DNA polymerases (Sambrook et al., 1989, Molecular Cloning: A Laboratory Manual, $2^{nd}$ edition, pp. 5.33–5.35, Cold Spring Harbor Laboratory, Cold Spring Harbor). The properties of the DNA polymerases, particularly the strand displacement activity of some of them, are given in detail by Kornberg and Baker, DNA Replication, $2^{nd}$ edition, pp. 113–225, Freeman, N.Y. (1992). Strand displacement is not a property common to all DNA polymerases since some of them, like T4 DNA polymerases, are not capable of accomplishing strand displacement alone. Strand displacement activity was shown initially for the Klenow fragment of *Escherichia coli* DNA polymerase I (Masamune and Richardson, 1971, *J. Biol. Chem.* 246: 2692–2701), which confers on this enzyme the capability of initiating replication of nucleic acid from the 3'OH end of a cleavage site in a double-stranded DNA. This strand displacement activity has also been shown in thermostable DNA polymerases such as Tli DNA polymerase (Kong et al., 1993. *J. Biol. Chem.* 268: 1965–1975). In this case it has also been shown that mutated forms of this enzyme do not have exonuclease 5'-3' activity that has a higher strand displacement capacity. This strand displacement activity has also been shown for T7 DNA polymerase (Lechner et al., 1983. *J. Biol. Chem.* 258: 11174–11184) and for HIV reverse transcriptase (Huber et al., 1989, *J. Biol. Chem.* 264: 4669–4678).

Preferably, a DNA polymerase with no exonuclease 5'-3' activity is used to accomplish the amplification cycle according to the invention since the effectiveness of the strand displacement activity is greater in enzymes with no such exonuclease activity. The Klenow fragment of *Escherichia coli* DNA polymerase I is an example of a polymerase with no exonuclease 5'-3' activity, as are polymerases such as T7 DNA polymerase or Sequenase (US Biochemical). T5 DNA polymerase or Phi29 DNA polymerase can also be used. However, a DNA polymerase having this exonuclease 5'-3' activity can be used when it does not prevent the amplification process from being carried out. In this case, the yield of the amplification reaction can be improved by specific inhibition of the exonuclease 5'-3' activity of DNA polymerases under the reaction conditions employed.

The present amplification process requires a reverse transcription step when the starting product is an RNA. This conversion step, of RNA into cDNA can also be accomplished by using reverse transcriptase such as AMV (avian myeloblastosis virus) or MMLV (Moloney murine leukemia virus), both available commercially. Any other enzyme with RNA- or DNA-dependent DNA polymerase activity can be used in the present invention provided it has strand displacement activity. In the contrary case, the strand displacement activity can be conferred by an inducer agent, activity of the helicase type, or Rec A. The properties of Rec A, particularly in the process of single-stranded DNA reassociation, strand capture, or strand assimilation are described in detail by McEntee and Weinstock in "The Enzymes," vol. XIV, pp. 445–470. The reverse transcription step can for example be accomplished with *Escherichia coli* DNA polymerase I as it has been shown that this enzyme also has RNA-dependent DNA polymerase activity (Ricchetti and Buc, 1993. *EMBO* 12: 387–396). For this purpose, RNA- and/or DNA-dependent thermostable DNA polymerases such as Taq polymerase or Tth polymerase can also be used; for a survey of the properties of thermostable DNA polymerases, see Rolf et al., PCR: Clinical Diagnostics and Research, pp. 224–258, Springer-Verlag, Heidelberg (1992).

Because of the utilization of the properties of RNAase H and chimeric primers as described, the present invention does not require endonuclease or exonuclease activity to initiate strand displacement by DNA polymerase.

Likewise, contrary to a number of amplification methods, the present invention does not require temperature cycles or chemical denaturing to dissociate the strand newly synthesized from its template. In this method, a single temperature can be employed as soon as initial denaturing of the target, if any, has been effected. This must be sufficient for the hybridization conditions authorizing specific hybridization of the primers on the target to be sufficiently discriminating. This temperature may for example be between 37° C. and 50° C. with conventional enzymatic reagents but may be higher (for example 50° to 80° C.) if thermostable enzymes are used.

A number of particular embodiments of the invention will now be described, referring to the attached drawings as applicable. In these drawings, a straight-line segment represents a nucleic acid fragment of the DNA type and a wavy line segment represents a nucleic acid fragment of the RNA type. An arrow (→) or a half-arrow (⇀ or ⇁) symbolizes the 3' end. The sign // indicates the possible existence of an upstream or downstream part not shown. The pairs of strands (or strands and primer segments) shown parallel are of course hybridized.

DETAILED DESCRIPTION OF PREFERRED EMBODIMENTS

Figure 1:
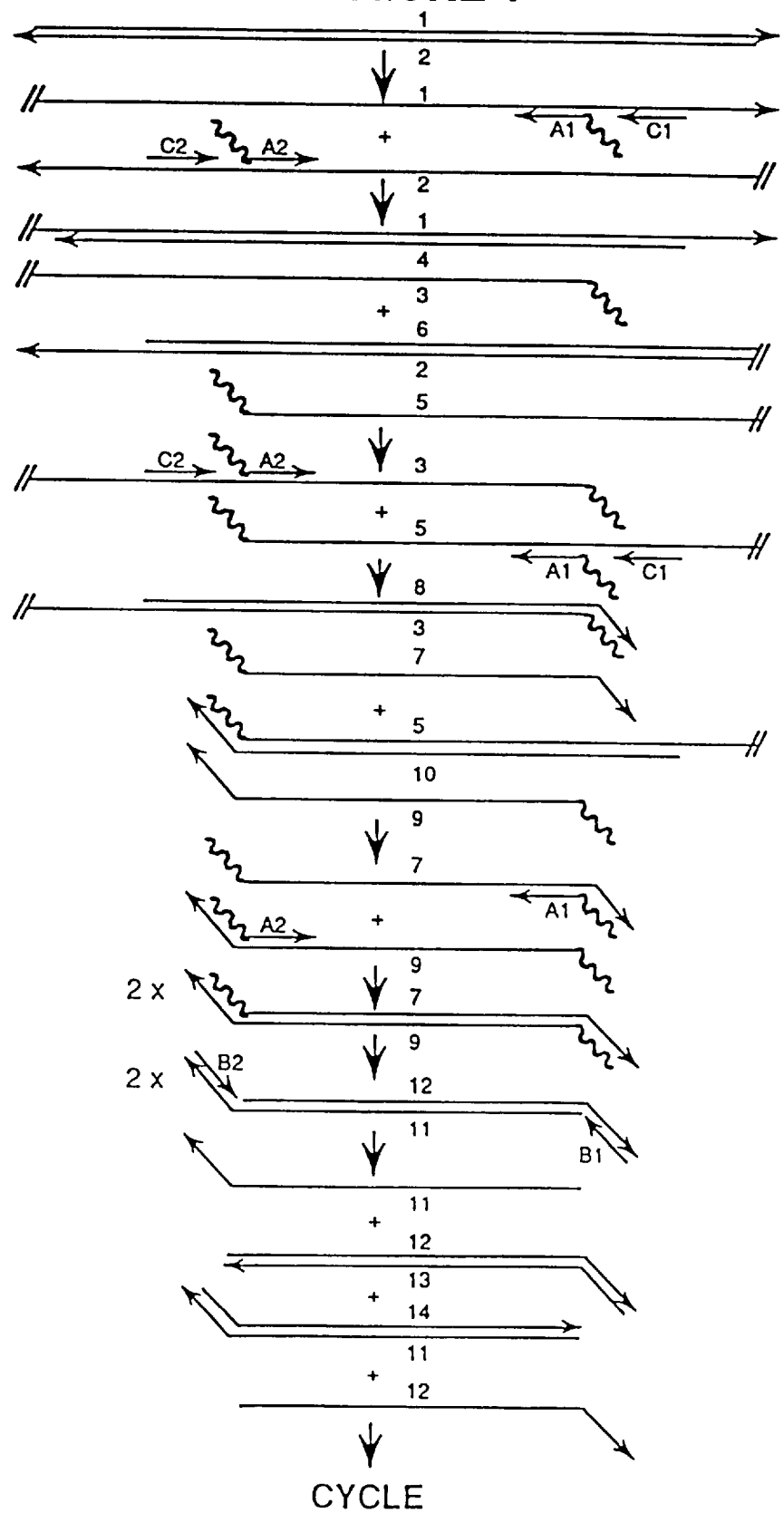
FIG. 1 shows one pathway of entry for the amplification process of the invention from single- or double-stranded DNA using a set of primers containing two type A (A1 and A2) chimeric primers corresponding to the first and second primers, two type B (B1 and B2) displacement primers corresponding to the third and fourth primers, and two other type C (C1 and C2) displacement primers corresponding to the fifth and sixth primers. The B and C primers are DNA-type sequence primers while the A primers are chimeric primers as defined and, in the example proposed, do not contain a second DNA-type segment.

According to a first embodiment of the invention, primers A1 and A2 do not contain the optional DNA type sequence at their 5' ends. After initial denaturing of the target nucleic acid assumed here to be in the form of a 1,2 double strand, primers A1, C1 on the one hand and A2, C2 on the other hand hybridize on their respective nucleic acid strands (FIG. 1). It should be noted that the starting product of FIG. 1 could be a DNA-RNA heteroduplex. Simultaneous extension of the primers in the presence of excess deoxyribonucleoside triphosphates and a DNA polymerase (RNA- and/or DNA-dependent, depending on whether the target is DNA or RNA) leads to displacement of the DNA 3 strand coming from elongation of A1 by extension of strand 4 from C1 and displacement of strand 5 coming from elongation of A2 by extension of strand 6 coming from C2. Primers A2 and C2, and A1 and C1, respectively, can then hybridize on single-stranded DNAs 3 and 5 obtained by extension of the A1 primers on the one hand and A2 on the other hand. Extension of C1 (producing strand 10) causes displacement of strand 9 synthesized from primer A1 and extension of C2 (producing strand 8) causes displacement of strand 7 synthesized from primer A2. The two strands 7 and 9, of defined length and thus released, are perfectly complementary and can hybridize on each other or hybridize with the A2 primer (strand corresponding to extension of A1) or A1 primer (strand corresponding to extension of A2), although hybridization of these short strands is favored thermodynamically.

Extension of A1 and A2 on their respective complementary strands 7 and 9 then leads to a double-stranded chimeric polynucleotide (7,9) of defined length, each of the strands consisting of a chimeric strand consisting of the target sequence to be amplified or its complementary strand, and also containing:

at its 5' end, an RNA-type segment with a homologous sequence to the RNA-type segment sequence of one or other of primers A1 or A2, depending on the strand considered, at its 3' end, a DNA-type segment with a complementary sequence to the sequence of the RNA-type segment of one or other of primers A1 or A2, depending on the strand considered.

The double-stranded chimeric polynucleotide obtained above is a substrate of ribonuclease H (or RNAase H). RNAase H allow selected degradation of an RNA-type segment in a DNA/RNA heteroduplex. Hence, after digestion by the nuclease, a double-stranded polynucleotide as defined above is obtained in which the RNA-type segment is degraded on at least one of the two strands. This double-stranded polynucleotide 11,12 then has at the 3' end of at least one of its strands a single-stranded DNA sequence which includes a complementary sequence of the B1 or B2 primer, depending on the strand considered. After hybridization of primers B1 and/or B2 on their respective targets, these primers are extended by DNA polymerase, causing displacement of the DNA strand located upstream of said primers. The 12,13 and/or 11,14 double strands are obtained, releasing the single-stranded 11 and/or 12 products that contain the sequence to be amplified (or its complementary) at which constitute the single-stranded polynucleotides that can be used as the point of departure of the amplification cycle according to the invention.

Figure 6:
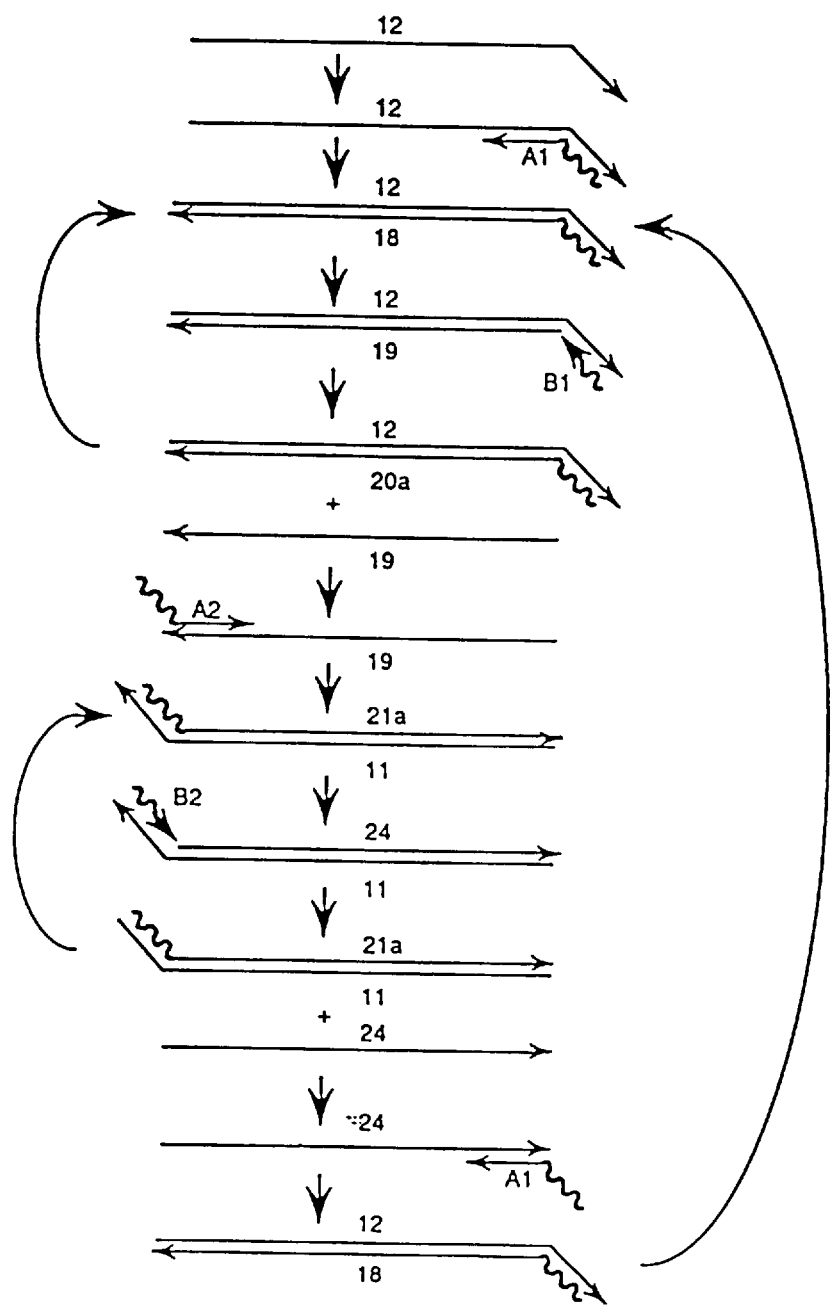
FIG. 6 shows a variant of the cyclic amplification flowchart of FIG. 5 in the case that the B1 and B2 displacement primers are made of RNA.

Advantageously, the B1 and/or B2 primers are of the RNA type. In this case, in the presence of excess B1 and/or B2 primers, as shown in FIG. 6, it is possible to increase the number of copies that can be obtained on the basis of a single hybridization of the A2 and/or A1 primer. It should be noted that strands 7 and 9 can also hybridize with primers B1 and B2 respectively, and it can easily be verified that, here again, release of single strands 11 and 12 is obtained.

Figure 2:
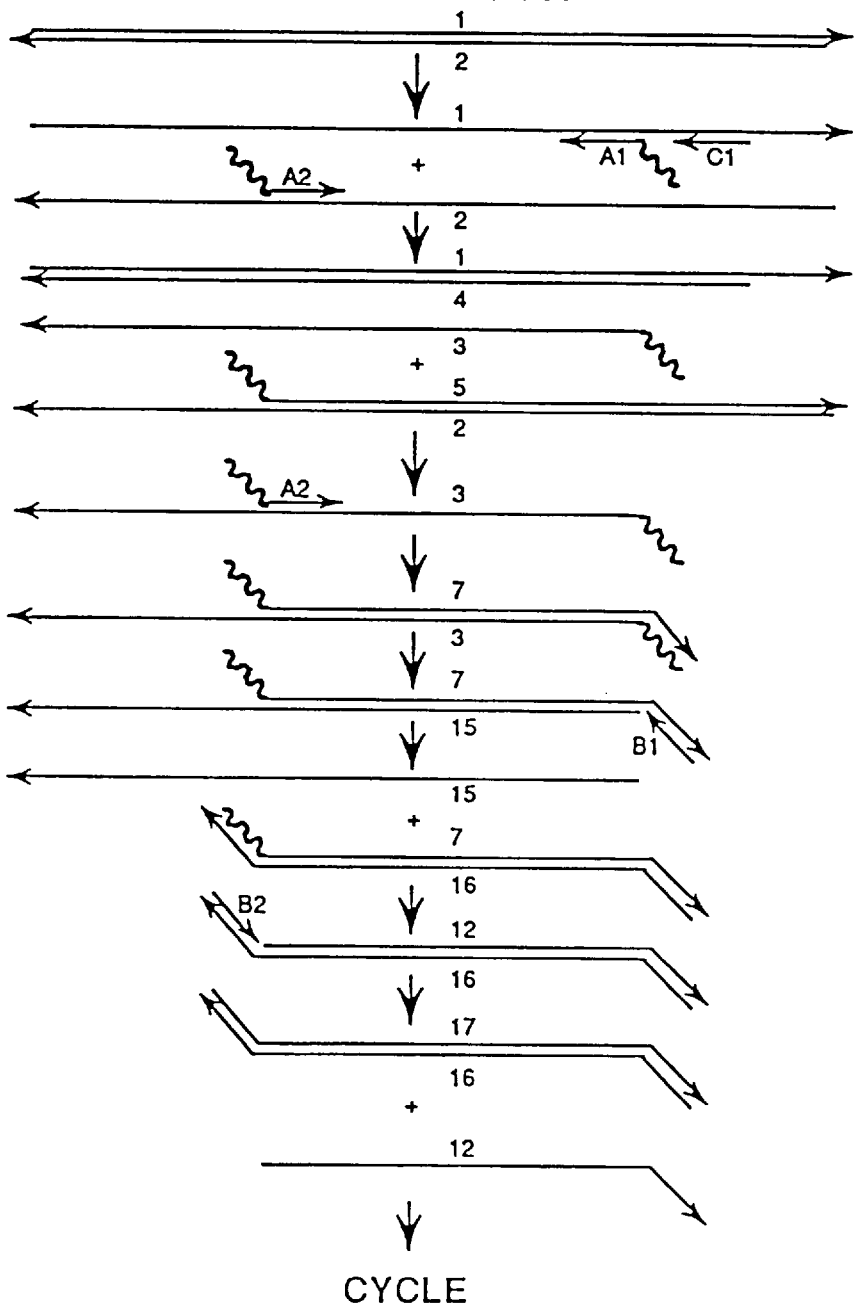
FIG. 2 shows a variant of the pathway of entry presented above using a set of primers which is as defined above but contains a single type C displacement primer.

It is easily observed that the pathway of entry previously presented can also be accomplished by using only the C1 or C2 primer associated with primers A1 and A2, and possibly B1 and/or B2. In this case (FIG. 2) after initial denaturing of the 1,2 target nucleic acid, hybridization of primers A1 and/or A2 and C1 or C2, and finally extension by DNA polymerase, only strand 3, coming from extension of A1, is displaced by synthesis of strand 4 coming from C1 (or only the strand coming from extension of A2 will be displaced by extension of the strand coming from C2). Single strand 3 can then hybridize with primer A2. Extension of this primer leads to formation of a 3,7 double-stranded molecule which has in particular, at one of its ends, an RNA/DNA heteroduplex segment. After digestion by RNAase H, hybridization of primer B2 or B1, respectively, and extension, single-stranded polynucleotide 12, which contains the sequence to be amplified, or its complementary, and which can be used as a starting point of the amplification cycle according to the invention, is released by formation of duplex 16,17.

Figure 3:
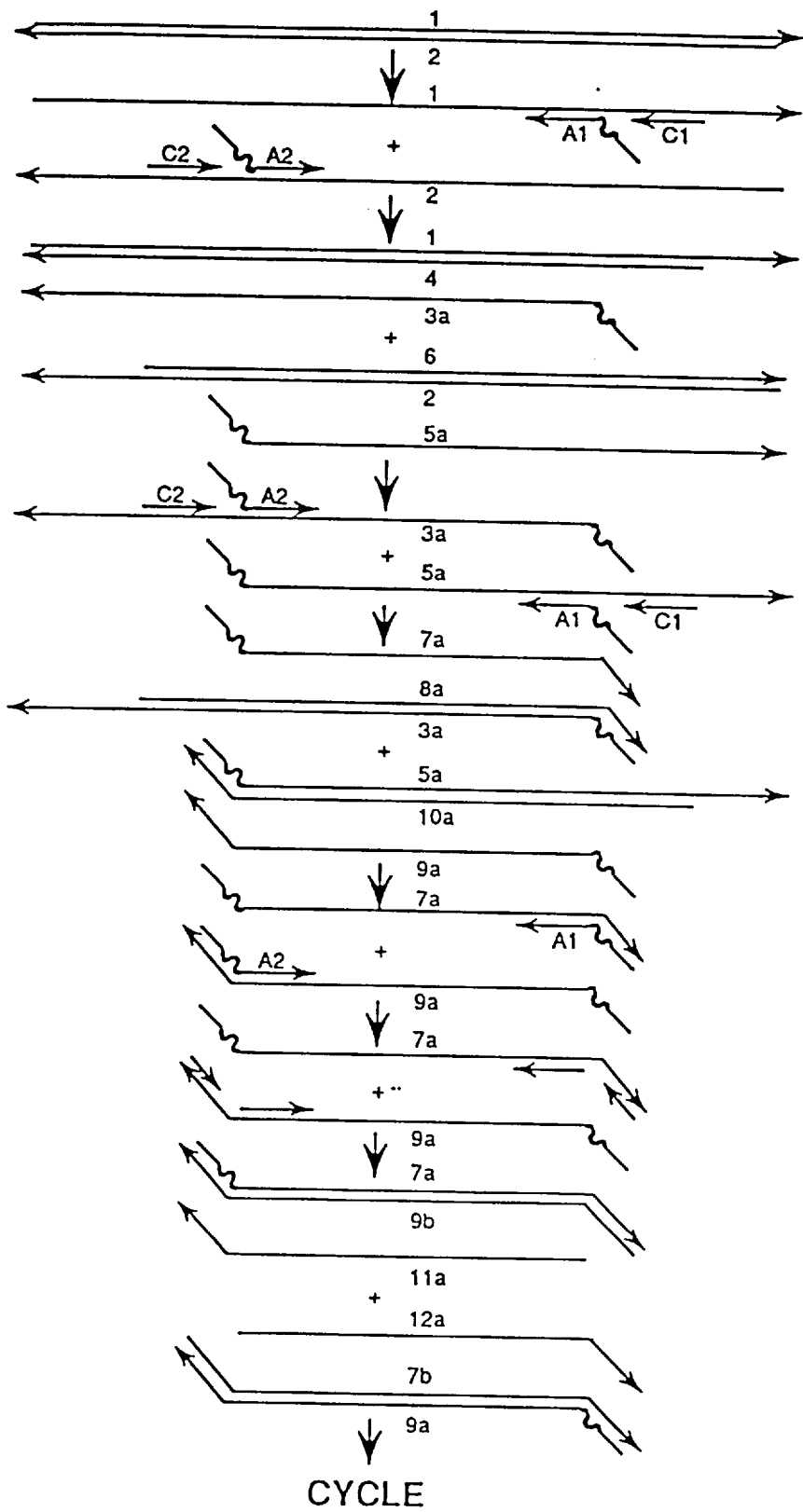
FIG. 3 shows another variant of the pathway of entry on a DNA target employing A primers containing an optional DNA-type segment at their 5' ends.

According to another embodiment of the invention, primers A1 and A2 have, at their 5' ends, upstream of the RNA-type segment, a DNA-type segment of defined sequence. As shown in FIG. 3, this characteristic, without modifying the actual principle of the invention, allows the use of primers B1 and B2 to be eliminated. This is because, when the RNA-type segment of primer A1 or A2, hybridized at its target, is digested under the action of ribonuclease H, it is easy to observe that the DNA-type A"1 segment coming from primer A1 (or A"2 coming from primer A2) can fulfill the function of the displacement primer B1 (or B2) described in the previous embodiments.

Figure 4:
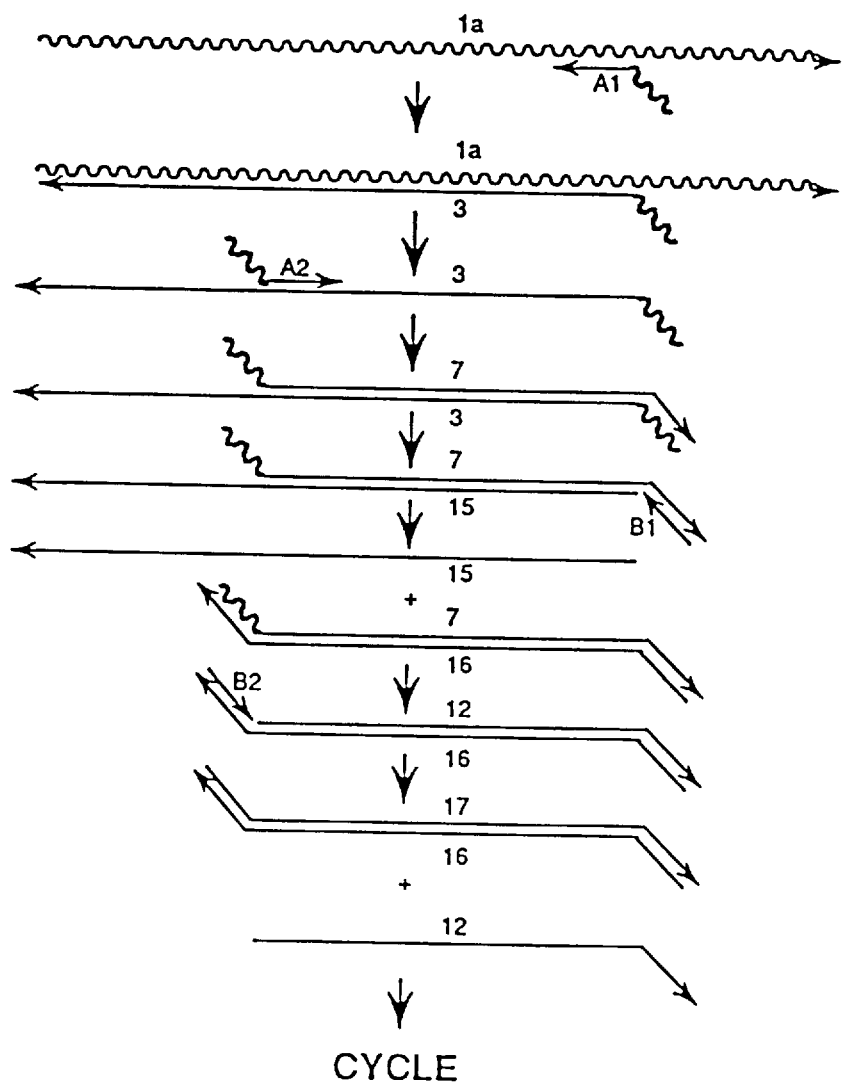
FIG. 4 represents a pathway of entry of the amplification method according to the invention from an RNA target using a set of primers containing only two type A chimeric primers and two type B displacement primers.

It is also interesting to note that, when the starting nucleic acid is a single-stranded RNA, the use of primer C1 or C2 is no longer required. As shown in FIG. 4, after hybridization and extension of primer A1 for example along strand 1a, the RNA template is degraded by the RNAase H, releasing a DNA-type single strand 3 which is capable of hybridizing with primer A2. As described above, alternate utilization of polymerization activities associated with displacement and digestion by RNAase H in the presence of primers A1 and A2, and possibly B1 and/or B2, leads to single-stranded polynucleotides that contain the sequence to be amplified, or its complementary sequence, which will be used as the starting point in the amplification cycle according to the invention. FIG. 4 shows that the reaction diagram very rapidly becomes identical to that of FIG. 2. This feature can be used when it is desired specifically to amplify a given sequence included in a ribonucleic acid (RNA) which can also be included, in the original reaction medium, in a deoxyribonucleic acid (DNA). In this case, merely omitting the C1 and/or C2 primer in the reaction medium will lead to amplification specificity according to the nature, DNA or RNA, of the target. In other words, in the absence of C1 or C2, it will be possible to amplify the target sequence only if it is present in the RNA form in the sample studied, and amplification will not occur if this target sequence is present only in the DNA form. It should also be noted that it is possible to hybridize a DNA type nucleic probe on the starting RNA in order to define a 5' RNA end. Because of hybridization of this probe, known as the locking probe, and digestion by RNAase H, it is possible to define precisely the point up to which extension of primer A1 can be accomplished.

The pathways of entry described above can also be effected from a target captured by means of a probe attached to a solid substrate. This probe can be immobilized covalently or passively as described in French Patent No. 91 09057 and International Patent WO 91/19812. This probe immobilization can also be effected by means of (co) polymers, particularly an N-vinylpyrrolidone copolymer, to which probes are coupled in the form of a conjugate, said conjugate being immobilized on a solid substrate by passive adsorption. More particularly, primers A1 and/or A2, and C1 and/or C2, can be attached to a solid substrate provided this attachment is not effected by the 3' end of the primers, so that the 3' end of these primers is capable of extension by a DNA polymerase in the presence of deoxyribonucleoside triphosphates. In addition, all or part of the A1 and C1 primers on the one hand and A2 and C2 primers on the other hand can be connected to each other by any linking arm (a hydrocarbon, a nucleotide, or other), from their 5' end, in order to control and balance the respective quantities of A1 relative to C1 on the one hand and A2 relative to C2 on the other hand, in the amplification reaction described.

Figure 5:
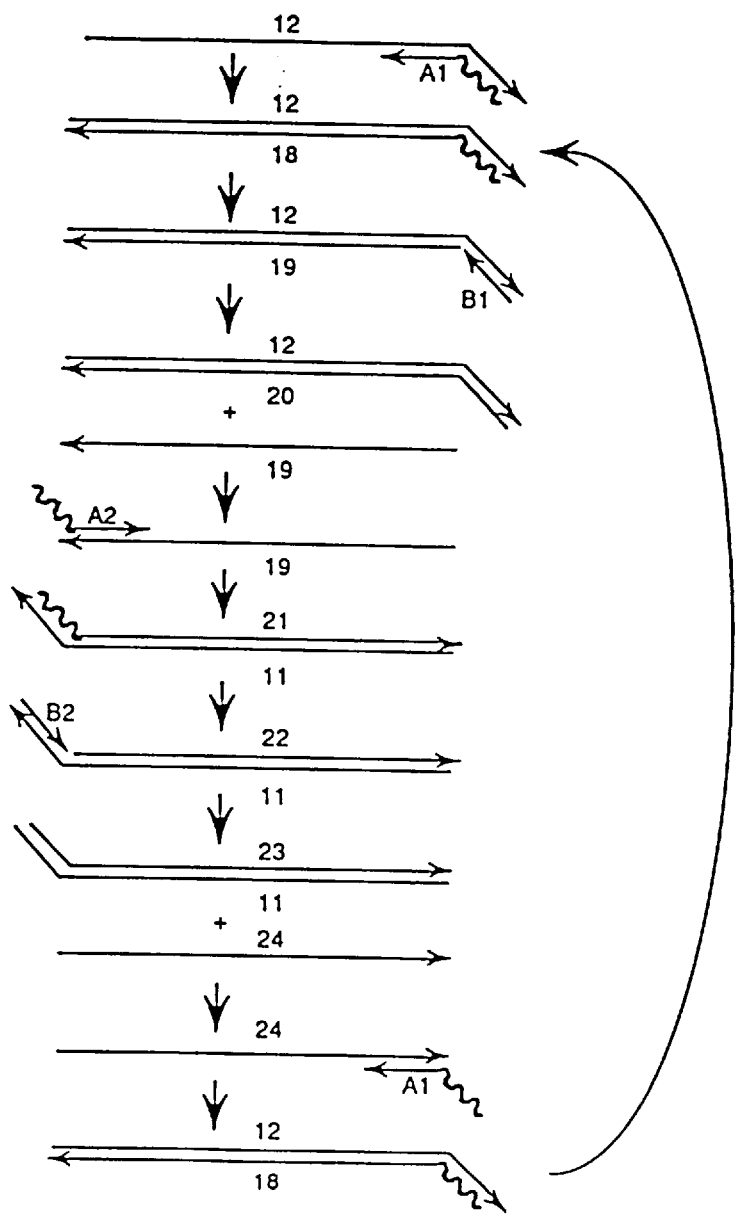
FIG. 5 is a flowchart of cyclic amplification obtainable with the process of the invention.

The single-stranded polynucleotide 11 that has been released (FIG. 1) can hybridize with primer A2. Likewise, the single-stranded polynucleotides such as 12 or 12a, released, can as before hybridize with primer A1 (FIG. 5). After extension of the primer by DNA polymerase forming the double strand 18,12 and digestion by ribonuclease H, primer B1 can once again hybridize on 12 and form the double strand 20, 12 and, by means of displacement activity, at the same time release the single-stranded DNA sequence 19 corresponding to the sequence that is to be amplified and on which primer A2 can be hybridized. By an analogous pattern using primer B2, the single-stranded 24 is obtained and extension of A1 leads once more to the double-stranded 18,12.

Since the DNA coming from one of the two pathways of the amplification method described (FIG. 5) is a substrate for the second pathway, and vice versa, it thus appears that the method according to the invention is a cyclic amplification technique.

It can be seen from the diagram of FIG. 6 that hybridization of A1 on 12 leads to the double strand 12,19 as before. Hybridization of primer B1, made of RNA this time, leads to displacement of strand 19 with formation of duplex 12,20a which is similar or identical to 12,18. Hybridization of A1 on 19 leads to duplex 11,21a (similar or identical to 11,21) and the action of RNAase H furnishes duplex 11,24. Hybridization of probe B2 (RNA) releases 24 in the form of a single strand with re-formation of duplex 11,21a. Hybridization of A1 on 24 leads to duplex 12,18 and so forth.

Thus, in the course of time, several amplification reaction cycles may occur until the reagents such as nucleoside triphosphates and primers are exhausted, leading to amplification whose yield corresponds to $10^9$ to $10^{12}$ molecules of DNA produced for a single initial target molecule. Depending on the concentrations of the reagents used, particularly the various primers, production of one or other of the strands of the starting target nucleic acid can be favored by the amplification method.

Implementation of the process according to the invention can be followed, if desired, by stages in which reaction products are separated and/or detected by various known methods. The separation methods include, among others, magnetic separation, and capture on a solid substrate, on a membrane, a filter, or a polymer. In each method, a capture residue can be attached to a magnetic ball, a membrane, a filter, or a polymer. The balls, membrane, solid substrate, filter, or polymer can then be tested for the presence or absence of the amplification product. The capture residues can, for example, be a sequence of nucleic acid complementary to the amplification reaction product, proteins or antibodies directed against a ligand, or a hapten incorporated into one of the primers used, or into the amplification product. The separation system can be coupled to the detection system, or not. Various detection methods can be used. One of them consists of detecting the reaction products with a size defined by electrophoretic separation. The methods vary according to the separation process, which can involve separation on gel, or attachment on various solid phases (balls, microtitration plate, latex, or magnetic particles). Another method labels a detection probe with a radioisotope such as $^{32}P$ for example then detects the radioactivity emitted by the reaction products, in combination with electrophoresis or not. Another method consists of chemically modifying an oligonucleotide primer by adding a ligand (biotin or digoxigenin, for example), an enzyme (alkaline phosphatase, peroxydase, or β-galactosidase, for example), a fluorescent label (phyccbiliprotein, fluorescein or rhodamine for example), a luminescent label (an acridinium ester for example), or a combination of these modifications. Another method consists of using a nucleotide detection primer that will hybridize on the amplification reaction product and will be elongated by a polymerase in the presence of ribonucleoside triphosphates (this primer can in this case also be modified as described above). The detection systems useful for reducing the invention to practice include homogeneous systems (namely, not requiring a separation system) and, by contrast, heterogeneous systems. In each system, one or more detectable labels are used and the reaction or emission of the detection system is measured, by automated apparatus for example. Examples of homogenous detection systems include fluorescence energy transfer, hybridization protection (acridinium luminescence), fluorescence polarization, and immunologic detection of a cloned enzyme donor. Examples of heterogeneous systems include enzymatic labels (peroxidase, phosphatase, β-galactosidase), fluorescent labels (enzymatic labels, rhodamine, fluorescein), and chemoluminescent or bioluminescent systems. In these detection systems, the detectable labels can be conjugated with a capture residue or the amplification products can be generated in the presence of a protein that can be recognized by a ligand or an antibody that can be recognized by a hapten.

The process of the invention can also be used as a method for indirect detection of a molecule of interest in which a polynucleotide, used as a label coupled with the molecule of interest, is amplified. The amplification products of the marker polynucleotide can themselves be detected directly by incorporation, when they are synthesized, of modified nucleotides such as those labeled with [$^{32}P$] or with [$^{3}H$] or can also be detected indirectly by the methods described above.

Another application of the process of the invention is obtaining an amplification product usable as a probe, or usable as a template for determining its nucleotide sequence. The amplified products can be separated from the enzymes used for amplification so that they can be used in later processes involving other enzymatic reactions, other amplification systems, sequencing methods, or nucleic acid synthesis methods, to cite only a few examples.

The invention also relates to a process of amplifying a target DNA sequence in which at least one RNA primer complementary to a downstream zone of the target sequence is used in the presence of nucleoside triphosphates and an enzyme system having DNA polymerase activity with displacement and RNAase H activity. Extension of the primer, followed by its digestion by RNAase, furnishes a duplex formed by the target DNA and a complementary DNA, with a defined 5' end. Further hybridization of the primer on this duplex leads to displacement of said complementary DNA strand at the 5' end defined with formation of the same duplex as above, and so forth. FIG. 6 contains an illustration of this process. This process can be used in particular to obtain multiple copies of a single strand of a double-stranded nucleic acid.

The following examples use the invention without however limiting it. Unless they are specified, all the methods for conducting the experiments described in the examples below were performed as described by Sambrook et al. (1989, Molecular Cloning: A Laboratory Manual, $2^{nd}$ edition, Cold Spring Harbor Laboratory, Cold Spring Harbor).

EXAMPLE 1

Synthesis of RNA/DNA Chimeric Oligonucleotides

The chimeric oligonucleotides RDC-1 (SEQ ID 3) and RDC-12 (SEQ ID 4) are prepared on an Expedite synthesizer (Millipore). Synthesis occurs from 3' to 5' using phosphoramidite chemistry. The RNA part is done with rapid deprotection phosphoramidite ribonucleotides from the Perkin Elmer Company. They are protected at 2' by a ter-butyldimethylsilyl (t-BDMS) group, (Admf: . 401350, Gdmf: Ref 401351, Cibu: Ref 401352, and U: Ref 4013531. Since the DNA part is located at 3', synthesis of the chimeras starts on a substrate provided with a deprotection rapid-cleaving deoxyribonucleotide supplied by PerSeptive Biosystems. The synthesis substrates are DNA 1 μmol DMT-dG(tBPA)-CGP (Ref. GEN084184) and thymidine-CPG (Ref. GEN061530) columns.

The two synthesis cycles used are according to the manufacturer's instructions.

An ammonia in ethanol solution is used to cleave the chimera-substrate bond. This solution is obtain by mixing 3 volumes of an aqueous ammonia solution (Aldrich, Ref. 3:38818) with 1 volume of pure ethanol (Merck, Ref. 983).

Deprotection of the chimeric oligonucleotide, with the exception of the 2' hydroxyl groups of the RNA part, is effected in the same ammonia solution for 3 hours at 55° C.

After evaporation of the ammonia solution in a rotary evaporator, 1.5 mL of triethylamine trifluorohydrate (TEA 3HF, Aldrich, Ref. 344648) are added to deprotect the 2' hydroxyl groups. After 24 hours contact at room temperature while stirring, with TEA 3HF, 300 μL of water are added and the oligonucleotides are precipitated with butanol (Aldrich, Ref. 154679).

After precipitation, the chimera molecule is dried under vacuum in a rotary evaporator after which 1 mL of sterile water is added and it is purified by reverse-phase chromatography under the following conditions:

Preparation column on Ultrapore RPMC, Beckman
dp 5 μm 10*250 mm
Serial No. 238770

Buffers: A=0.1M ammonium acetate, pH 6.5
B=0.05M ammonium acetate/50% acetonitrile
References: Merck ammonium acetate (Ref. 11160500)
Acetonitrile: BAKER HPLC gradient grade
Gradient: 0 to 30% B in 45 minutes, flowrate 4.7 mL/min.
The chimeric oligonucleotide solutions are heated at 90° C. for 5 minutes then injected for HPLC.

EXAMPLE 2

Hybridization of a Chimeric Primer on Its Target, Digestion by RNAase H of the RNA Segment, Hybridtization of a Displacement Primer, and Extension of This Primer The purpose of this example is to show that after degradation by RNAase H of the RNA segment of a RNA/DNA chimeric primer previously hybridized on a DNA target, it is possible to hybridize a displacement primer (DNA or RNA) upstream of the DNA segment, which remains hybridized by the chimera, and to show that this displacement primer can serve as a substrate for a DNA polymerase with a view to its extension, the latter accompanied by displacement of the DNA segment from its chimera. Several oligonucleotides are used for this purpose. In a first series of experiments, the oligonucleotide RDC-6 (SEQ ID NO:1) constitutes the target DNA template, and oligonucleotide RDC-1 (SEQ ID NO:3) and oligonucleotide RDC-4 (SEQ ID NO:6) are the chimeric and displacement primers, respectively. In the second series, the target DNA template is noted RDC-13 (SEQ ID NO:2), the chimeric oligonucleotide is noted RDC-12 (SE: ID NO:4), and the displacement primer is still RDC-4 (SEQ ID NO:6). The sequences of oligonucleotides RDC-1 (SEQ ID NO:3) and RDC-12 (SEQ ID NO:4) are complementary to the oligonucleotide sequence RDC-6 (SEQ ID NO:1) and RDC-13 (SEQ ID NO:2), respectively. The RDC-4 oligonucleotide sequence (SEQ ID NO:6) is homologous with the sequence of the RNA segment of oligonucleotides RDC-1 (SEQ ID NO:3) and RDC-12 (SEQ ID NO:4). This RDC-4 oligonucleotide is radiolabeled with $^{32}$P at its 5'-OH end by polynucleotide kinase.

The oligonucleotide RDC-1 (SEQ ID NO:3) and oligonucleotide (RDC-6 (SEQ ID NO:1), or RDC-12 (SEQ ID NO:4) and RDC-13 (SEQ ID NO:2) are incubated for 1 minute at 95° C. at the concentration of 5·10$^9$ copies/μL each in a final volume of 20 μL of 50 mM Tris HCl reaction medium, pH 8.3, 75 mM KCl, 3 mM MgCl$_2$, 10 mM DTT, and containing 1 mM of each of the dNTPs. The tubes are then left to stand for 10 minutes at 37° C. to allow the oligonucleotides to hybridize, with the possible addition of 0.8 unit of RNAase H (thermostable RNAase, Epicentre Technologies) and/or 200 units of reverse transcriptase (Superscript II, Gibco-BRL). Reaction controls without enzyme and/or without template are performed in parallel. After incubation for 15 minutes at 37° C., the labeled oligonucleotide RDC-4 (SEQ ID NO:6) is added to the medium at the concentration of 5·10$^9$ copies/μL. Incubation at 37° C. is continued for 30 minutes and the reacticn is stopped by cooling on ice. Part of each sample (10 μL) is mixed with 10 μL of "formamide blue" (90% formamide, 0.02% xylene cyanol, 0.02% bromophenol blue, 25 mM EDTA) then analyzed by electrophoresis on 15% gel polyacrylamide—7M urea in the presence of a molecular weight label formed by a mixture of oligodeoxyribonucleotides with 70, 60, 40, 33, 25, 20, and 15 nucleotides. After drying, the gel is autoradiographed onto x-ray film.

Whatever the set of primers (RDC-1 and RDC-6 or RDC-12 and RDC-13), an extension product whose size (40 bases) corresponds to the extension of the labeled RDC-4 primer along the DNA target (RDC-6 or RDC-13, respectively) is observed when said RDC-4 primer is hybridized then elongated. This product is observable only in the presence of RNAase H and reserve transcriptase; in the absence of one of these enzymes, no extension product is detectable.

In a second series of experiments, the DNA-type displacement primer RDC-4 was replaced by the RNA-type displacement primer RDC-9 (SEQ ID NO:7). The operating conditions are identical to those described above. The results obtained with this RNA-type primer RDC-9 are comparable to those observed with the DNA-type primer RDC-4.

EXAMPLE 3

Use of a DNA/RNA/DNA Chimeric Primer

The purpose of this example is to show that the utilization of a more complex chimera with a DNA segment from 5' to 3' then an RNA segment, and finally a DNA segment, avoids using an additional displacement primer in the process according to the invention. Two oligonucleotides were used to accomplish this. Oligonucleotide RDC-6 (SEQ ID NO:1) is the target DNA template, and oligonucleotide RDC-10 (SEQ ID NO:5) is the chimeric primer. The oligonucleotide sequence RDC-10 (SEQ ID NO:5) is complementary to the oligonucleotide sequence RDC-6 (SEQ ID NO:1). Oligonucleotide RDC-10 is radiolabeled with $^{32}$P at its 5'-OH end by polynucleotide kinase.

Radiolabeled oligonucleotide RDC-10 and oligonucleotide RDC-6 are incubated for one minute at 95° C. at the concentration of $5 \cdot 10^9$ copies/$\mu$L each in a final volume of 20 $\mu$L of reaction medium as described in the preceding example. The tubes are then left to stand for 10 minutes at 37° C. to allow the oligonucleotides to hybridize. The reaction mixture is then deposited on nondenaturing polyacrylamide gel to recover specifically the duplex coming from hybridization of the RDC-10 and RDC-6 single strands and eliminate the nonhybridized labeled oligonucleotide RDC-10. After extraction of the purified material by electrophoresis followed by dialysis and precipitation, the nucleic acids are dissolved in 20 $\mu$L of 50 mM Tris HCl buffer, pH 8.3, 75 mM KCl, 3 mM MgCl$_2$, 10 mM DTT, and containing 1 mM of each of the dNTPs. 0.1 unit of RNAase H (thermostable RNAse, EPI Center Technologies) and 200 units of reverse transcriptase (Superscript II, Gibco-BRL) are then added. Reaction controls without enzyme and/or without template are conducted in parallel. After incubation for 30 minutes at 37° C., the reaction is stopped by cooling on ice. Part of each sample (10 $\mu$L) is mixed with 10 $\mu$L "formamide blue" (90% formamide, 0.02% xylene cyanol, 0.02% bromophenol blue, 25 mM EDTA) then analyzed by electrophoresis on 15% gel polyacrylamide—7M urea in the presence of a molecular weight label formed by a mixture of oligodeoxyribonucleotides with 70, 60, 40, 33, 25, 20, and 15 nucleotides. After drying, the gel is autoradiographed onto x-ray film.

The results observed show that the oligonucleotide RDC-10 indeed hybridizes with the target oligonucleotide RDC-6 and that this duplex is a substrate for RNAse H (control without reverse transcriptase but in the presence of RNAse H and appearance of a radiolabeled product with approximately 15 bases). In addition, the results show that, after degradation of all or part of the RNA segment of the RDC-10 chimera, the DNA segment of the chimera, that has remained hybridized at the 3' end of the target RDC-6, is used as a primer by polymerase (a radiolabeled product with 40 bases is obtained).

EXAMPLE 4

In a first series of experiments, this example shows than an RNA primer hybridized on a DNA target may serve as a substrate for a DNA polymerase for its extension, then for RNAse H for its degradation; in a second series of experiments, it shows that digestion by RNAse H of the RNA segment included in a DNA/RNA chimeric primer prehybridized on a DNA target allows hybridization on the DNA target of an RNA-type displacement primer whose extension by a DNA polymerase is accompanied by displacement of the DNA strand coming from the chimeric primer. This process may be repeated a large number of times by degrading the RNA part of the extension product of the displacement primer then hybridizing a new primer, elongating this primer with displacement of the hybridized strand downstream, and so forth.

In the first series of experiments, an RNA displacement primer RDC-8 (SEQ ID NO:8) hybridized on the target DNA template RDC-6 (SEQ ID NO:1) serves as a substrate for the Klenow fragment of DNA polymerase I USB) that has no 3'-5' and exonuclease 5'-3' activity. $10^{11}$ copies of the RDC-6 oligonucleotide (SEQ ID NO:1) are incubated for 5 minutes at 65° C. then 3 minutes at 37° C. in the reaction medium described above in Example 2 in the presence of 1 mM dATP, dTTP, dGTP, and 0.1 $\mu$M dCTP containing 1 $\mu$Ci [$\alpha$-$^{32}$P]. After addition of $2 \times 10^{11}$ copies of the RNA displacement primer RDC-8 (SEQ ID NO:8), incubation is continued in the presence of 10 U Klenow Exo$^-$ (USB) and/or 0.2 U of thermostable RNAse H (Epicentre Technologies) for 30 minutes at 37° C. The reaction is stopped by cooling on ice. Part of each sample (10 $\mu$L) is mixed with 10 $\mu$L formamide blue (90% formamide, 0.02% xylene cyanol, 0.02% bromophenol blue, 25 mM EDTA) then analyzed by electrophoresis on 15% polyacrylamide denaturing gel—7M urea for two hours at 350 volts in the presence of a molecular weight label formed of a mixture of oligodeoxyribonucleotides with 70, 60, 40, 33, 25, 20, and 15 nucleotides. The gel is analyzed by autoracliography on BioMax film (Kodak). In the presence of Klenow Exo$^-$, an extension product whose size (40 bases) corresponds to extension of displacement primer RDC-8 is observed. Addition of exogenous RNAse H to the reaction medium reveals a product with 20 bases corresponding to the extension product of primer RDC-8 in which the RNA fragment has been digested by RNAse H.

The second series of experiments is performed on a heteroduplex formed by hybridizing $2 \times 10^{11}$ copies of chimeric oligonucleotide RDC-1 (SEQ ID NO:3) hybridized on $10^{11}$ copies of target DNA template RDC-6 (SEQ ID NO:1), in the presence of $2 \times 10^{11}$ copies of displacement primer RDC-8 (SEQ ID NO:8) under experimental conditions identical to those described above. In the presence of Klenow Exo$^-$, no product corresponding to extension of displacement primer RDC-8 (SEQ ID NO:8) is observed because in this case the hybridization site of primer RDC-8 is not accessible on DNA target RDC-6 (SEQ ID NO:1). When 0.2 U of RNAse H is added to the reaction medium, a product with 20 bases corresponding to the size of the extension product digested by RNAse H is observed. This experiment shows that the RNA segment of chimeric primer RDC-1 can be digested by RNAse H, and an RNA displacement primer RDC-8 can be hybridized and elongated by the Klenow Exo$^-$, displacing the remaining DNA from the chimera. This leads to reconstitution of the RDC-1/RDC-6 duplex. The phenomenon can be repeated. Thus, in the extension product of the first displacement primer, the RNA can in its turn be digested by RNAse H, rendering the hybridization site accessible to another RDC primer (in excess). This leads to accumulation of radiolabeled products with 20 bases by repeating the digestion-hybridization-extension process.

EXAMPLE 5

In this example, we look at reconstitution of an RNA/DNA heteroduplex by elongating a DNA primer on a chimeric oligonucleotide in the presence of a DNA polymerase, digestion by RNAse H of the RNA part of the newly synthesized duplex, followed by extension of a DNA displacement primer hybridizing on the site released by digestion. In this experiment, the RNA/DNA heteroduplex is reconstituted in the presence of the Klenow fragment of *E. coli* DNA polymerase I. A mixture is made of $10^{13}$ copies of DNA primer A18 (SEQ ID NO:9) and $10^{13}$ copies of chimera RDC-12 (SEQ ID NO:4) in 20 μL of a 50 mM Tris-HCl, pH 7.5, 10 mM $MgCl_2$, 1 mM DTT reaction medium in the presence of 1 mM of each dNTP. The tubes are left for 3 minutes at 65° C. then 5 minutes at 37° C. with the addition of 5 U Klenow (Boehringer Mannheim). The reaction is allowed to proceed for 30 minutes at 37° C. and is stopped by cooling on ice. The products are purified by extraction with a phenol-chloroform-isoamyl alcohol mixture and concentrated by filtration on a Microcon 3 unit (Amicon). They are assayed by absorbance at 260 nm. The products, in $3 \times 10^{12}$ copies, obtained are incubated in the reaction medium 50 mM Tris-HCl (pH 7.5), 10 mM $MgCl_2$, 1 mM DTT in the presence of 1 mM dARP, dGTP, and dTTP and 0.1 μM dCTP containing 0.5 μCi of [α-$^{32}$P] for 3 minutes at 65° C. then 5 minutes at 37° C. The displacement primer RDC-4 ($10^{12}$ copies) is added to the reaction and incubation proceeds in the presence of 5 U Klenow fragment (Boehringer Mannheim) in the presence or absence of 0.2 U of thermostable RNAse H (Epicentre Technologies) for 30 minutes at 37° C. In parallel, extension controls are run under the same conditions in the presence of $10^{12}$ copies of displacement primer RDC-4 hybridized on $10^{12}$ copies of synthetic target RDC-13 (SEQ ID NO:2) whose sequence is complementary to the RDC-12 chimera sequence (SEQ ID NO:4). The reaction products are analyzed as described in the first series of experiments of Example 4. Autoraciographic analysis of the controls reveals an extension product whose size (40 bases) corresponds to extension of displacement primer RDC-4 (SEQ ID NO:6) on target RDC-13 (SEQ ID NO:2). In the presence of the reconstituted heteroduplex, the same extension product appears intensely if RNAse H and the Klenow fragment are present in the medium.

---

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: CHEMICAL SYNTHESIS ( x i ) SEQUENCE DESCRIPTION: SEQ ID NO:1:

CTCTTACTGT  CATGCCATCC  GTCTCGTCTC  GTCTCGTCTC  40

( 2 ) INFORMATION FOR SEQ ID NO:2:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: CHEMICAL SYNTHESIS ( x i ) SEQUENCE DESCRIPTION: SEQ ID NO:2:

ACACTGCGGC CAACTTACTT GTCTCGTCTC GTCTCGTCTC 40

( 2 ) INFORMATION FOR SEQ ID NO:3:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "RNA- DNA CHIMERA"

( i i i ) HYPOTHETICAL: NO ( i v ) ANTI-SENSE: NO ( v i ) ORIGINAL SOURCE:
        ( A ) ORGANISM: CHEMICAL SYNTHESIS ( i x ) FEATURE:
        ( A ) NAME/KEY: misc_feature
        ( B ) LOCATION: 1..20
        ( D ) OTHER INFORMATION: /note= "NUCLEOTIDES 1 TO 20 ARE
            RIBONUCLEOTIDES - NUCLEOTIDES 21 TO 40 ARE
            DEOXYRIBONUCLEOTIDES"

( x i ) SEQUENCE DESCRIPTION: SEQ ID NO:3:

GAGACGAGAC GAGACGAGAC GGATGGCATG ACAGTAAGAG 40

( 2 ) INFORMATION FOR SEQ ID NO:4:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "RNA- DNA CHIMERA"

( i i i ) HYPOTHETICAL: NO ( i v ) ANTI-SENSE: NO ( v i ) ORIGINAL SOURCE:
        ( A ) ORGANISM: CHEMICAL SYNTHESIS ( i x ) FEATURE:
        ( A ) NAME/KEY: misc_feature
        ( B ) LOCATION: 1..20
        ( D ) OTHER INFORMATION: /note= "NUCLEOTIDES 1 TO 20 ARE
            RIBONUCLEOTIDES - NUCLEOTIDES 21 TO 40 ARE
            DEOXYRIBONUCLEOTIDES"

( x i ) SEQUENCE DESCRIPTION: SEQ ID NO:4:

GAGACGAGAC GAGACGAGAC AAGTAAGTTG GCCGCAGTGT 40

( 2 ) INFORMATION FOR SEQ ID NO:5:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA- RNA-DNA CHIMERA"

( i i i ) HYPOTHETICAL: NO ( i v ) ANTI-SENSE: NO (v i) ORIGINAL SOURCE:
         (A) ORGANISM: CHEMICAL SYNTHESIS (i x) FEATURE:
         (A) NAME/KEY: misc_feature
         (B) LOCATION: 16..20
         (D) OTHER INFORMATION: /note= "NUCLEOTIDES 16 TO 20 ARE
             RIBONUCLEOTIDES - OTHER NUCLEOTIDES ARE
             DEOXYRIBONUCLEOTIDES"

(x i) SEQUENCE DESCRIPTION: SEQ ID NO:5:

GAGACGAGAC GAGACGAGAC GGATGGCATG ACAGTAAGAG        40

(2) INFORMATION FOR SEQ ID NO:6:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
         (A) ORGANISM: CHEMICAL SYNTHESIS (x i) SEQUENCE DESCRIPTION: SEQ ID NO:6:

GAGACGAGAC GAGACGAG        18

(2) INFORMATION FOR SEQ ID NO:7:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (i i) MOLECULE TYPE: RNA (genomic)

(i i i) HYPOTHETICAL: NO (i v) ANTI-SENSE: NO (v i) ORIGINAL SOURCE:
         (A) ORGANISM: CHEMICAL SYNTHESIS (x i) SEQUENCE DESCRIPTION: SEQ ID NO:7:

GAGACGAGAC GAGACGAG        18

(2) INFORMATION FOR SEQ ID NO:8:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (i i) MOLECULE TYPE: RNA (genomic)

(i i i) HYPOTHETICAL: NO (i v) ANTI-SENSE: NO (v i) ORIGINAL SOURCE:
         (A) ORGANISM: CHEMICAL SYNTHESIS (x i) SEQUENCE DESCRIPTION: SEQ ID NO:8:

GAGACGAGAC GAGACGAGAC        20

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: CHEMICAL SYNTHESIS ( x i ) SEQUENCE DESCRIPTION: SEQ ID NO:9:

A T A A C A C T G C   G G C C A A C         1 7

We claim:

1. A method for amplifying a target nucleic acid sequence, said sequence comprising, starting from its 5' end, an upstream region, and, starting from its 3' end, a downstream region, said method comprising the steps of:
obtaining a DNA-type single-stranded polynucleotide comprising a first segment corresponding to the target sequence to be amplified and at least a second segment of arbitrary sequence located downstream of the 3' end of said first segment; and placing said single-stranded polynucleotide in contact with an excess amount of a set of primers, in the presence of an enzyme system with DNA-dependent DNA polymerase activity, strand displacement activity, and RNAse H activity, and in the presence of an excess amount of deoxyribonucleotide triphosphates such that said target nucleic acid sequence is amplified, said set of primers comprising at least one primer selected from the group consisting of:

1) a first chimeric primer comprising successively, in the 5'→3' direction: an RNA-type segment with a sequence complementary to at least a portion of said second segment of said single-stranded polynucleotide, said portion comprising at least the 5' end of said second segment, and a DNA-type segment capable of hybridizing with at least a portion of said downstream region, said portion comprising at least the 3' end of said downstream region, and 2) a second chimeric primer comprising successively, in the 5'→3' direction: an RNA-type segment of arbitrary sequence, and a DNA-type segment homologous with at least a portion of said upstream region, said portion comprising the 5' end of said upstream region, wherein:
either the first primer further comprises, upstream of the RNA-type segment, a second DNA-type segment of arbitrary sequence having a 3' end capable of hybridizing with the 3' end of said polynucleotide when said RNA segment is shorter than said second segment of said single-stranded polynucleotide, or the first primer does not comprise such a second DNA-type segment, then said set of primers further comprises a third primer comprising a 3' end capable of hybridizing with at least a portion of said second segment of said single-stranded polynucleotide, and wherein:
either the second primer further comprises, upstream of the RNA-type segment, a second DNA-type segment of arbitrary sequence, or the second primer does not comprise such a second DNA-type segment, then said set of primers further comprises a fourth primer comprising a 3' end that is homologous with at least a portion of the sequence of the RNA-type segment of the second primer.

2. The method according to claim 1, wherein said set of primers comprises said first and second primers that do not comprise a second DNA-type segment, and said third primer and fourth primers.

3. The method according to claim 1, wherein said third and fourth primers are of the DNA type.

4. The method according to claim 1, wherein said third and fourth primers are of the RNA type.

5. The method according to claim 1, wherein said obtaining a DNA-type single-stranded polynucleotide comprises providing a starting product which is a nucleic acid comprising the sequence to be amplified and further comprising, beyond the 3' end of said sequence, a downstream polynucleotide segment that comprises a downstream zone, said method further comprising adding a fifth primer capable of hybridizing with said downstream zone.

6. The method according to claim 5, wherein the starting product comprising the sequence to be amplified further comprises, beyond the 5' end of said sequence, an upstream polynucleotide segment.

7. The method according to claim 6, wherein a sixth primer homologous with an oligonucleotide zone of said upstream polynucleotide segment is added.

8. The method according to claim 1, wherein said obtaining a DNA-type single-stranded polynucleotide comprises providing a starting product which is an RNA comprising the sequence to be amplified, and placing said starting product in contact with at least one primer from the set of primers.

9. The method according to claim 8, wherein said RNA is placed in contact with said first primer and second primer.

10. The method according to claim 9, wherein said set of primers further comprises at least one of said third primer and said fourth primer.

11. A method according to claim 1, wherein said set of primers comprises said first primer and said second primer.

12. A method according to claim 1, wherein said set of primers further comprises at least one of said third and said fourth primers.

13. A kit for implementing a process of amplification of a target nucleic acid sequence, wherein said kit comprises an enzyme system with RNAse H activity and at least one chimeric primer comprising successively, in the 5'→3' direction:

an optional segment, of the DNA type, a segment of the RNA type, and a segment of the DNA type, wherein said kit further comprises an enzyme system having DNA-dependent DNA polymerase activity and strand displacement activity.

* * * * *